(12) United States Patent
Ramachandran et al.

(10) Patent No.: US 9,040,764 B2
(45) Date of Patent: *May 26, 2015

(54) CATALYST FOR METATHESIS OF ETHYLENE AND 2-BUTENE AND/OR DOUBLE BOND ISOMERIZATION

(71) Applicant: Lummus Technology Inc., Bloomfield, NJ (US)

(72) Inventors: Bala Ramachandran, Easton, PA (US); Sukwon Choi, Clifton, NJ (US); Robert J. Gartside, Brewster, MA (US); Marvin I. Greene, Clifton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,613

(22) Filed: Nov. 11, 2013

(65) Prior Publication Data

US 2014/0066681 A1    Mar. 6, 2014

Related U.S. Application Data

(62) Division of application No. 12/506,615, filed on Jul. 21, 2009, now Pat. No. 8,586,813.

(51) Int. Cl.
*C07C 5/25* (2006.01)
*B01J 21/08* (2006.01)
(Continued)

(52) U.S. Cl.
CPC .............. *C07C 5/2512* (2013.01); *B01J 21/08* (2013.01); *B01J 21/10* (2013.01); *C07C 6/04* (2013.01); *C07C 2521/04* (2013.01); *C07C 2521/08* (2013.01); *C07C 2521/10* (2013.01); *C07C 2521/16* (2013.01); *C07C 2523/02* (2013.01); *C07C 2523/04* (2013.01); *C07C 2523/30* (2013.01)

(58) Field of Classification Search
USPC .................. 585/324, 326, 329, 330, 670, 671
See application file for complete search history.

(56) References Cited

U.S. PATENT DOCUMENTS 2,947,708 A * 8/1960 Wilson, Jr. .................... 502/234
3,915,897 A   10/1975 Reusser et al.
4,684,760 A    8/1987 Drake
(Continued)

FOREIGN PATENT DOCUMENTS

| EP | 0251351 A2 | 1/1988 |
| WO | 9012645 A1 | 11/1990 |
| WO | 2008153643 A1 | 12/2008 |

OTHER PUBLICATIONS

Search and Examination Report dated May 10, 2014 in corresponding GCC Patent Application No. GC2010-16330 (8 pages).

(Continued)

*Primary Examiner* — Prem C Singh
*Assistant Examiner* — Sharon Pregler
(74) *Attorney, Agent, or Firm* — Osha • Liang LLP

(57) ABSTRACT

A process for the double-bond isomerization of olefins is disclosed. The process may include contacting a fluid stream comprising olefins with a fixed bed comprising an activated basic metal oxide isomerization catalyst to convert at least a portion of the olefin to its isomer. The isomerization catalysts disclosed herein may have a reduced cycle to cycle deactivation as compared to conventional catalysts, thus maintaining higher activity over the complete catalyst life cycle.

15 Claims, 5 Drawing Sheets

(51) Int. Cl.
*B01J 21/10* (2006.01)
*C07C 6/04* (2006.01)

(56) References Cited

U.S. PATENT DOCUMENTS

| | | | |
|---|---|---|---|
| 4,814,542 A | | 3/1989 | Forlani et al. |
| 4,970,191 A | | 11/1990 | Schutz |
| 4,992,612 A | * | 2/1991 | Suzukamo et al. ........... 585/664 |
| 5,087,780 A | | 2/1992 | Arganbright |
| 5,120,894 A | | 6/1992 | McCauley |
| 5,153,165 A | | 10/1992 | Lowery et al. |
| 5,300,718 A | * | 4/1994 | McCaulley ................... 585/324 |
| 5,898,091 A | | 4/1999 | Chodorge et al. |
| 6,075,173 A | | 6/2000 | Chodorge et al. |
| 6,358,482 B1 | | 3/2002 | Chodorge et al. |
| 6,580,009 B2 | | 6/2003 | Schwab et al. |
| 6,683,019 B2 | | 1/2004 | Gartside et al. |
| 6,727,396 B2 | | 4/2004 | Gartside |
| 6,777,582 B2 | | 8/2004 | Gartside et al. |
| 6,875,901 B2 | | 4/2005 | Gartside et al. |
| 7,074,976 B2 | * | 7/2006 | Powers et al. ................. 585/324 |
| 7,214,841 B2 | | 5/2007 | Gartside et al. |
| 7,223,895 B2 | | 5/2007 | Sumner |
| 7,351,393 B1 | | 4/2008 | Bayense et al. |
| 8,178,737 B2 | * | 5/2012 | Leyshon ....................... 585/328 |
| 2005/0014981 A1 | | 1/2005 | Gartside et al. |
| 2005/0043574 A1 | | 2/2005 | Powers et al. |
| 2008/0312481 A1 | | 12/2008 | Leyshon |
| 2010/0056839 A1 | | 3/2010 | Ramachandran et al. |
| 2010/0286458 A1 | | 11/2010 | Iselborn et al. |

OTHER PUBLICATIONS

Office Action issued Apr. 15, 2014 in corresponding Chinese application No. 201080010848.2 (11 pages).
Office Action issued Mar. 11, 2014 (w/translation) in corresponding Korean application No. 10-2012-7004101 (11 pages).
Examination Report issued Aug. 15, 2014 in corresponding Singapore application No. 2011077997 (13 pages).
Substantive Examination Report issued Dec. 22, 2014 in corresponding Philippines application No. 1/2011/501937 (1 page).
Search and Examination Report dated Nov. 30, 2014 in corresponding GCC Patent Application No. GC2010-16330 (7 pages).
Correspondence reporting an Office Action issued Dec. 1, 2014 in corresponding Chilean application No. 2118-2011 (13 pages).
Office Action issued Sep. 8, 2014 in corresponding Canadian application No. 2,748,877 (2 pages).
Rejection Decision (w/translation) issued Nov. 3, 2014 in corresponding Chinese application No. 201080010848.2 (18 pages).
Notice of Decision to Refuse a Patent (w/translation) issued Sep. 30, 2014 in corresponding Korean patent application No. 10-2012-7004101 (5 pages).
Office Action issued Sep. 10, 2014 in corresponding Canadian patent application No. 2,826.975 (2 pages).
Notification of Reasons for Refusal (w/translation) issued Sep. 9, 2014 in corresponding Japanese application No. 2013-196913 (7 pages).
Substantive Examination Adverse Report issued Jan. 15, 2015 in corresponding Malaysia application No. PI2011004068 (3 pages).
International Search Report and Written Opinion issued Feb. 21, 2011 in International application No. PCT/US2010/040528 (8 pages).
Office Action issued Jul. 30, 2012 in corresponding Canadian application No. 2,748,877 (3 pages).
Extended European Search Report dated Dec. 11, 2012 in corresponding European application No. 10802634.5 (15 pages).
A. Ozaki: "The effective site on acid catalysts revealed in n-butene isomerization". Journal of Catalysis, vol. 3, No. 5, Oct. 1, 1964; pp. 395-405 (11 pages).
Kenneth J. Klabunde et al.: "A comparison of electron donor and proton abstraction activities of thermally activated pure magnesium oxide and doped magnesium oxides", Journal of the America Chemical Society, vol. 109, No. 4, Feb. 1, 1987, pp. 1111-1114 (4 pages).
Office Action issued Jun. 25, 2013 (w/translation) in corresponding Japanese application No. 2012-501037 (9 pages).
Office Action issued Dec. 10, 2013 in corresponding Canadian application No. 2,748,877 (4 pages).

* cited by examiner

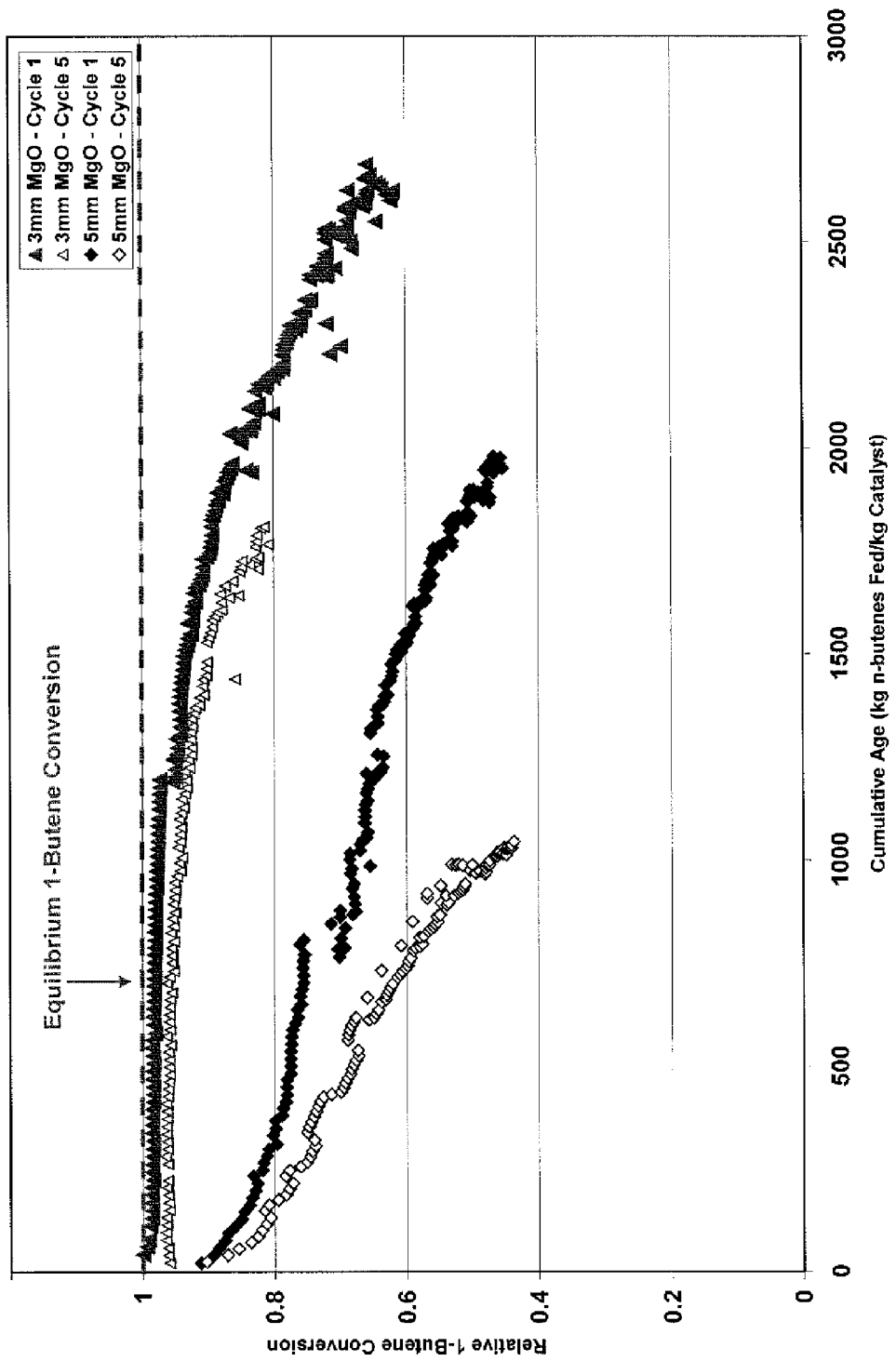

CATALYST FOR METATHESIS OF ETHYLENE AND 2-BUTENE AND/OR DOUBLE BOND ISOMERIZATION

CROSS-REFERENCE TO RELATED APPLICATIONS

This application is a divisional application and claims benefit under 35 U.S.C. §120 to U.S. patent application Ser. No. 12/506,615, filed Jul. 21, 2009, issued as U.S. Pat. No. 8,586,813, on Nov. 19, 2013, which is incorporated by reference in it's entirety.

FIELD OF THE DISCLOSURE

Embodiments disclosed herein relate generally to the processing of a $C_3$ to $C_6$ hydrocarbon cut from a cracking process, such as steam or fluid catalytic cracking, primarily for conversion of $C_4$ olefins to propylene via metathesis. More specifically, embodiments disclosed herein relate to a catalyst for the metathesis of ethylene and 2-butene and/or isomerization of 1-butene to 2-butene or isomerization of 2-butene to 1-butene, depending upon equilibrium.

BACKGROUND

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadiene, iso- and normal butenes, and iso- and normal butane can be processed in many ways. A typical steam cracker $C_4$ cut contains the following components in weight %:

TABLE 1

Typical $C_4$ cut components and weight percentages.

| | |
|---|---|
| $C_4$ Acetylenes | Trace |
| Butadiene | 33% |
| 1-butene | 15% |
| 2-butene | 9% |
| Isobutene | 30% |
| Iso- and Normal Butanes | 13% |

Typically, the butadiene and $C_4$ acetylenes are removed first. This can be accomplished by either hydrogenation or extraction. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system changing the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for downstream operations. The butenes remaining in the mixture consist of normal olefins (1-butene, 2-butene) and iso-olefins (isobutene). The balance of the C4's in the mixture consists of both iso- and normal-butanes from the original feed plus what was produced in the hydrogenation steps and any small quantity of unconverted or unrecovered butadiene.

The butenes have many uses, and in many processes it is desirable to have isomerization of double bonds within a given molecule. Double bond isomerization is the movement of the position of the double bond within a molecule without changing the structure of the molecule. This is different from skeletal isomerization where the structure changes (most typically representing the interchange between the iso-form and the normal form). Skeletal isomerization proceeds by a completely different mechanism than double bond isomerization. Skeletal isomerization typically occurs using a promoted acidic catalyst.

Double bond isomerization is an equilibrium limited reaction. For the equilibrium between 1 butene and 2-butene (cis and trans), the interior olefin (2 butene) is favored at lower temperatures. Starting with either pure butene-1 or pure butene-1 or mixtures thereof, the reaction will move to the equilibrium ration of butene-2 to butene-1. There are two primary reaction routes. One is hydroisomerization where the reaction occurs over typically a noble metal catalyst in the presence of hydrogen at lower temperature and the other is non-hydroisomerization where the reaction occurs generally at higher temperatures over basic metal oxide catalysts and no hydrogen is used.

Double bond hydroisomerization can occur in a hydrogenation reactor. The hydroisomerization reaction uses small quantities of hydrogen over noble metal catalysts (such as Pt or Pd) and occurs at moderate temperatures while the latter is hydrogen free and typically employs basic metal oxide catalysts at higher temperatures. Double bond hydroisomerization usually takes place at moderate temperatures to maximize the interior olefin (2-butene for example as opposed to 1-butene) as the thermodynamic equilibrium favors the interior olefin at lower temperatures. This technology is usually preferred when there is a need to produce an internal olefin for a downstream process. Ethylenolysis of 2-butene to make propylene is such a reaction. The ethylenolysis (metathesis) reaction is 2-butene+ethylene→2 propylenes. Mixed normal butenes (1- and 2-butenes) are typically used as the feed for the metathesis reaction and hydroisomerization is employed upstream of the metathesis reaction to maximize 2-butene in the feed.

However, double bond isomerization can also occur independently without the use of hydrogen in either an independent isomerization reactor or in conjunction with metathesis and typically employs basic metal oxide catalysts at higher temperatures. While interior olefins remain the predominant normal butene in the mixture as the temperature is increased, the formation of the alpha olefin (1 butene) by equilibrium is increased. The use of the basic metal oxide catalyst in the absence of hydrogen eliminates the production of the paraffin by hydrogenation that would result from a hydroisomerization system.

Ethylenolysis (metathesis) of 2 butene occurs at high temperature for example 300 C over a metathesis catalyst. However, only 2-butene participates in this metathesis reaction. The metathesis reaction of 1-butene with ethylene is considered to be a non-productive reaction as the products of this metathesis reaction are essentially the same as the reactants. Therefore, it is advantageous to convert as much of the 1-butene to 2-butene, simultaneously during metathesis to thus maximize the production of propylene. Under these conditions, non-hydroisomerization is employed and typically the basic metal oxide isomerization catalyst is physically mixed with the metathesis catalyst to allow both reactions to proceed simultaneously.

Conventional metathesis with isomerization involves the reaction of mixed normal butenes (both 1-butene and 2-butene) with ethylene to produce propylene, as described above. These reactions occur in the presence of a group VIA or VITA metal oxide metathesis catalyst, either supported or unsupported in combination with basic metal oxide isomerization catalysts. Typical catalysts for metathesis are tungsten oxide supported on silica or rhenium oxide supported on alumina. Examples of catalysts suitable for the metathesis of olefins are described in U.S. Pat. No. 6,683,019, for example.

However, it is common to employ a double bond isomerization catalyst within the metathesis reactor to shift 1-butene to 2-butene and allow for continued reaction. Typical double bond isomerization catalysts include basic metal oxides (Group IIA), either supported or unsupported. Hydroisomerization is particularly not preferred since at the elevated temperatures of the reaction, the required hydrogen would saturate some fraction of the olefin reactants to paraffins thus reducing the product yields. For example, U.S. Pat. No. 6,875,901 discloses a process for the isomerization of olefins using a basic metal oxide catalyst, such as a high purity magnesium oxide catalyst, which may be in the form of powder, pellets, extrudates, and the like. Magnesium oxide and calcium oxide are examples of such double bond isomerization catalysts that may be physically admixed with the metathesis catalyst. No equivalent co-catalyst exists for the skeletal isomerization of isobutene to normal butene. In the case of a conventional metathesis system employing both a metathesis catalyst and a co-mixed double bond isomerization catalyst, the butadiene must be removed to a level of less than 500 ppm to avoid rapid fouling of the double bond isomerization catalyst. The metathesis catalyst itself can tolerate butadiene levels up to 10,000 ppm.

Isobutene is typically removed from the feedstock prior to the metathesis reaction step. The reaction of isobutene with ethylene is non-productive and metathesis reaction with itself and/or other $C_4$'s is limited in the presence of excess ethylene. Non-productive reactions essentially occupy catalyst sites but produce no product. If allowed to remain in the feed to the metathesis unit, the concentration of this non-reactive species would buildup creating capacity limitations. Options for isobutene removal include reacting it with methanol to produce methyl tertiary butyl ether (MTBE) or separating the isobutene from the butenes by fractionation. U.S. Pat. No. 6,358,482 discloses the removal of isobutene from the $C_4$ mixture prior to metathesis. This scheme is further reflected in U.S. Pat. Nos. 6,075,173 and 5,898,091. U.S. Pat. No. 6,580,009 discloses a process for the production of propylene and hexene from a limited ethylene fraction. For molar ratios of ethylene to butenes (expressed as n-butenes) from 0.05 to 0.60, a raffinate II stream is used as the $C_4$ feedstock. A raffinate II stream is by definition a stream following isobutene removal. Isobutene removal from the $C_4$ stream may also be accomplished by employing a combined catalytic distillation hydroisomerization deisobuteneizer system to both remove the isobutene and recover n-butenes at high efficiency by isomerizing the 1-butene to 2-butene, as described in U.S. Pat. No. 5,087,780.

High temperature double bond isomerization catalysts are also used for double bond isomerization alone, not in the presence of a metathesis catalyst and/or ethylene. For example, 1-butene is a valuable co-monomer for the production of certain grades of polyethylene. 1-Butene can be produced via the isomerization of 2 butene coupled with fractionation as described in U.S. Pat. No. 6,875,901. Furthermore as described in U.S. Pat. No. 6,727,396, such an isomerization catalyst is useful in the isomerization of internal hexene isomers (2 and 3 hexene) to 1-hexene. 1-hexene is also a valuable co-monomer for polyethylene. In this case, the metathesis takes place between 1 butene and itself (1 butene+1 butene→ethylene+3 hexene). This reaction uses similar metathesis catalysts as referenced above but critically, the feed to the metathesis step must be highly concentrated 1 butene. The basic metal oxide isomerization catalyst is used as described in U.S. Pat. No. 6,875,901 to produce the stream of highly concentrated 1 butene. The 1 butene is then subjected to metathesis alone specifically avoiding a isomerization function in that step. The resultant 3 hexene is then subjected to a separate high temperature—non hydroisomerization double bond isomerization step. The advantage of such isomerization is the favorable equilibrium at higher temperatures for the alpha olefin and the lack of hydrogen present to hydrogenate olefins to paraffins.

The metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced. Typical guard bed adsorbents are alumina and or activated alumina. It is also possible to use basic metal oxides such as magnesium oxide and/or calcium oxide as guard bed materials. At low temperatures, they have the capacity to adsorb water and react with oxygenates such as methanol to form water and carbon dioxide. The water formed is subsequently adsorbed by the other basic oxide sites.

Metathesis reactions are very sensitive to the location of the olefin double bond and the stereo-structure of the individual molecules. A pair of olefins adsorbs on the surface and exchange double bond positions with the carbon groups on either sides of the double bonds. Metathesis reactions can be classified as productive, half productive or non-productive. As described above, non-productive reactions result in essentially no reaction taking place. When the double bonds shift with metathesis reaction, the new molecules are the same as the originally adsorbed molecules thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation, when the double bonds shift, new products are formed. Alternately if they adsorb in a different steric configuration, when the bonds shift, the identical olefins are formed and thus no new products are formed. The various metathesis reactions proceed at different rates (a fully productive reaction is usually faster than a half productive reaction) and with different weight selectivities to propylene.

Table 2 summarizes the reactions between ethylene and various butenes and the reactions between the butenes themselves.

The reactions listed represent the base reaction with ethylene (reaction 1, 4 and 5) as well as the reactions between the various $C_4$ olefins. It is especially important to make a distinction between the selectivity to propylene from total $C_4$ olefins (including isobutene) and the selectivity to propylene from the normal $C_4$ olefins involved in the reaction. The reaction of isobutene with 2-butene (reaction 6) produces propylene and a branched $C_5$ molecule. For this reaction, propylene is produced at 37.5 weight % selectivity from total $C_4$'s (similar to reaction 2) but at a 75 weight % selectivity from normal $C_4$'s (2-butene). For the purposes of definitions, conventional metathesis is defined as the reaction of the $C_4$ olefin stream with ethylene. However, the $C_4$ stream can also react in the absence of ethylene as a feedstock. This reaction is called auto or self metathesis. In this case, reactions 2, 3, 6, and 7 are the only possible reactions and will occur at rates dependent upon the feedstock composition.

TABLE 2

| No. | Reaction | Type | Rate | Wt. % Selectivity ($C_3H_6$ from total $C_4$s) | Wt. % Selectivity ($C_3H_6$ from n-$C_4$s) |
|---|---|---|---|---|---|
| 1 | 2-butene + ethylene → 2 propylene (Conventional Metathesis) | Fully Productive | Fast | 100 | 100 |
| 2 | 1-butene + 2-butene → Propylene + 2-pentene | Fully Productive | Fast | 37.5 | 37.5 |
| 3 | 1-butene + 1-butene → Ethylene + 3-hexene | Half Productive | Slow | 0 | 0 |
| 4 | Isobutene + Ethylene → No reaction | Non-productive | No Reaction | — | — |
| 5 | 1-butene + ethylene → No reaction | Non-productive | No Reaction | — | — |
| 6 | Isobutene + 2-butene → Propylene + 2-methyl 2-butene | Fully Productive | Fast | 37.5 | 75 |
| 7 | Isobutene + 1-butene → ethylene + 2-methyl 2 pentene | Half productive | Slow | 0 | 0 |

In conventional metathesis for propylene production, the focus is to maximize reaction 1 to produce propylene. This will maximize the selectivity to propylene. As such, excess ethylene is used to reduce the extent of the reactions of butenes with themselves (reactions 2, 3, 6, and 7). The theoretical ratio is 1/1 molar or 0.5 weight ratio of ethylene to n-butenes, but it is common in conventional metathesis to employ significantly greater ratios, typically, 1.3 or larger molar ratio to minimize reactions 2, 3, 6 and 7. Under conditions of excess ethylene, and due to the fact that both isobutene and 1-butene do not react with ethylene (see reactions 4 and 5), two process sequences are employed. First, the isobutene is removed prior to metathesis. If isobutene is not removed, it will buildup as the n-butenes are recycled to achieve high yield. Second, 1-butene is isomerized to 2-butene by including a double bond isomerization catalyst such as magnesium oxide admixed with the metathesis catalyst. Note that this catalyst will not cause skeletal isomerization (isobutene to normal butenes) but only shift the double bond from the 1 position to the 2 position. Thus by operating with excess ethylene, eliminating isobutene from the metathesis feed prior to reaction, and employing a double bond isomerization catalyst, reaction 1 is maximized.

As described above, magnesium oxide catalysts may be mixed with metathesis catalysts for performing both double-bond isomerization and metathesis in the same reactor. In such a system, the magnesium oxide serves two functions. First, the magnesium oxide acts as a guard bed, adsorbing various oxygenates and water to protect the metathesis catalyst. At the higher temperatures of the metathesis reaction, the capacity for adsorption is much lower than at temperatures closer to ambient but this function provides a valuable second poison adsorption step following the bulk poison removal via guard beds as mentioned above. Second, as described above, the reaction of ethylene with 1-butene is non-productive; as 1-butene essentially does not react with ethylene, 1-butene will buildup in the recycle stream. In order to avoid 1-butene buildup, double-bond isomerization catalysts, such as magnesium oxide, may be used to isomerize the 1-butene to 2-butene as the 2-butene is depleted during the reaction.

Double-bond isomerization catalysts, such as magnesium oxide, are currently commercially used in the form of tablets having an effective diameter of about 5 mm. As used herein, effective diameter refers to the diameter that non-spherical shaped particles would have if it were molded into a sphere. These tablets exhibit good isomerization activity when processing butenes alone. However, such tablets exhibit activity for isomerization of 1-butene to 2-butene only for a short time in the presence of ethylene. Further, their performance is progressively worse as the number of reaction cycles increase. After several regeneration/reaction cycles, their activity for isomerization is low. This performance shortfall may lead to a rapid buildup of 1-butene in the system over time, limiting reactor performance by hydraulically limiting the recycle, and limiting the overall conversion of butenes to propylene that can be obtained economically. A similar loss of activity is experienced when operating these catalysts as double bond isomerization catalysts alone for the production of the terminal olefin from the interior olefin.

It is well known in the industry that smaller sized catalyst particles exhibit better performance during the reaction cycles. This is due to the reduction of internal mass transfer resistance. This allows the reactants to have greater access to the catalyst sites. By reducing the mass transfer resistances, improved reactivity is achieved. However, the loss of activity with regeneration cycles is not improved. The loss of activity as a result of regenerations is due not to simple mass transfer limitations as a function of effective diameter but to the loss of surface area of the catalyst particle (of any size) due to sintering created by the higher temperatures required for coke removal for example.

Some attempts have been made to improve the performance of magnesium oxide catalysts. For example, U.S. Pat.

No. 6,875,901 discloses improvements to the deactivation rate of magnesium oxide isomerization catalysts by limiting certain impurities, such as phosphorous, sulfur, transition metals, etc. Deactivation in the presence of ethylene, however, remains problematic.

As described above, there remains a need for basic metal oxide double-bond isomerization catalysts that may improve the overall performance of the metathesis process, increasing propylene yield and decreasing 1-butene recycle purge. There is also a need for an improved version of these catalysts for the simple double bond isomerization of interior olefins to terminal olefins, for example butene-2 to butene-1 or hexene 2 or hexene-3 to hexene-1. For both of these systems there is a need to reduce the cycle to cycle deactivation thus maintaining higher activity over the complete catalyst life cycle.

SUMMARY OF THE DISCLOSURE

In one aspect, embodiments disclosed herein relate to a process for the double-bond isomerization of olefins, the process including: contacting a fluid stream comprising olefins with a fixed bed comprising an activated basic metal oxide isomerization catalyst comprising a structure stabilizing agent, to convert at least a portion of the olefin to its isomer.

In another aspect, embodiments disclosed herein relate to a process for the double-bond isomerization of olefins, the process including: contacting a fluid stream comprising olefins with a fixed bed comprising an activated basic metal oxide isomerization catalyst having an effective diameter in the range of 0.25 mm to 4.0 mm to convert at least a portion of the olefin to its isomer.

In another aspect, embodiments disclosed herein relate to a process for the production of propylene, including: fractionating a hydrocarbon stream comprising n-butenes, isobutene, and paraffins into at least two fractions including a light $C_4$ fraction comprising isobutene and a heavy $C_4$ fraction comprising n-butenes and paraffins; feeding ethylene and the heavy $C_4$ fraction to a fixed bed reactor comprising a metathesis catalyst and an activated basic metal oxide isomerization catalyst comprising a structure stabilizing agent, contacting the heavy $C_4$ fraction with the activated basic metal oxide isomerization catalyst to convert at least a portion of the 1-butene to 2-butene; and contacting ethylene and at least a portion of the 2-butene with a metathesis catalyst to form a metathesis product comprising propylene, paraffins, any unreacted ethylene, and any unreacted 1-butene and 2-butene.

In another aspect, embodiments disclosed herein relate to a process for the production of propylene, including: fractionating a hydrocarbon stream comprising n-butenes, isobutene, and paraffins into at least two fractions including a light $C_4$ fraction comprising isobutene and a heavy $C_4$ fraction comprising n-butenes and paraffins; feeding ethylene and the heavy $C_4$ fraction to a fixed bed reactor comprising a metathesis catalyst and activated basic metal oxide isomerization catalyst wherein the isomerization catalyst has an effective diameter between 0.25 and 4.0 mm and does not contain a stabilizing agent; contacting the heavy $C_4$ fraction with the activated basic metal oxide isomerization catalyst to convert at least a portion of the 1-butene to 2-butene; and contacting the ethylene and at least a portion of the 2-butene with a metathesis catalyst to form a metathesis product comprising propylene, paraffins, any unreacted ethylene, and any unreacted 1-butene and 2-butene.

Other aspects and advantages will be apparent from the following description and the appended claims.

BRIEF DESCRIPTION OF DRAWINGS

FIG. 5 is a graphical illustration of the comparison of 1-butene conversion over cumulative age for different particle size MgO catalysts in metathesis service for propylene for both initial and 5th cycles.

DETAILED DESCRIPTION

Figure 1:
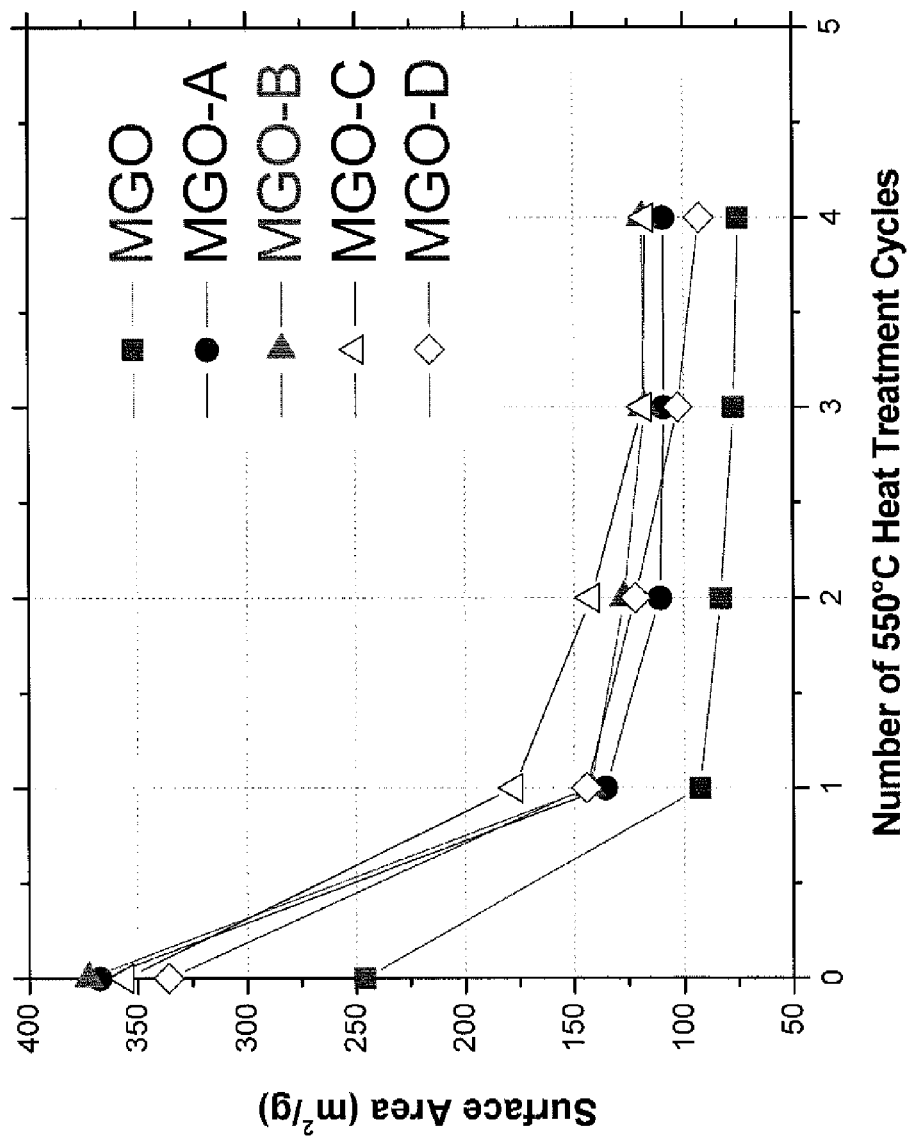
FIG. 1 is a graphical representation of changes in BET surface area of MgO tablets containing a structure stabilizing agent, as a function of thermal aging.

In one aspect, embodiments disclosed herein relate to the improvement in the stability of the isomerization catalyst surface area over multiple regenerations by the addition of a structure stabilizing agent. In another aspect, embodiments disclosed herein relate to the improvement in the stability of the isomerization catalyst surface area over multiple regenerations by the reduction of the effective diameter of the isomerization catalyst without the addition of a stabilizing agent.

In further aspects, embodiments disclosed herein relate generally to the processing of a $C_3$ to $C_6$ hydrocarbon cut from a cracking process, such as steam or fluid catalytic cracking, primarily for conversion of $C_4$ olefins to propylene via metathesis. More specifically, embodiments disclosed herein relate to a catalyst for the metathesis of ethylene and 2-butene and/or isomerization of internal olefins to terminal olefins for example 2-butene to 1-butene.

Useful isomerization catalysts may include basic metal oxides such as magnesium oxide, calcium oxide, barium oxide, strontium oxide, and lithium oxide, either individually or in combination. Other oxides, such as sodium oxide or potassium oxide may be incorporated into the catalyst as promoters. In certain embodiments, the catalyst for use in isomerization may be magnesium oxide (MgO). While certain aspects will be described herein in terms of magnesium oxide, it should be understood that the other basic metal oxides mentioned above are also contemplated as being within the scope of embodiments disclosed herein.

Magnesium oxide double bond isomerization catalysts undergo aging with thermal cycling (number of regeneration cycles). The effects of thermal cycling were examined for various MgO catalysts (for 5 mm tablets) using BET surface area and pore size determination and powder x-ray diffraction (XRD). Analysis of existing data shows that the MgO catalysts exhibit sintering (loss of surface area with increasing average pore diameter) with multiple regeneration cycle treatments.

XRD data also shows that the primary MgO peak becomes sharper with increasing cycles of regeneration. This indicates the average crystalline size of MgO increases with multi-cycle regeneration treatments based on average crystallite size estimates obtained from peak width measurements using the Debye-Scherer equation. The results show that multi-cycle regeneration leads to crystal growth. The growth of crystals results in loss of surface area thus the XRD data confirms the deactivation.

These analyses show that as the MgO catalyst undergoes multiple regeneration cycles, the BET surface area reduces significantly, with a corresponding increase in average crystallite size and average pore diameter. This physical deterioration of the catalysts over multiple cycles with intermittent regenerations, results in the deactivation of the catalyst activity for double bond isomerization. Progressively shorter cycle lengths are observed as a result of the physical deterioration of the MgO catalyst.

Silica was added using an aqueous silica binder solution that contains 30 wt. % $SiO_2$ (Ludox AS-30, Aldrich chemicals) on to 5 mm MgO tablets (MGO) to prepare MGO-A and MGO-B. Samples MGO-C and MGO-D were prepared by wet impregnation. Dry "as is" MgO pellets were added to a $SiO_2$ containing aqueous solution (Ludox+distilled water for MGO-C, or sodium silicate+distilled water for MGO-D). After the small amounts of excess liquid was removed, the wet pellets were oven-dried at 120° C. for 24 hours.

Multiple BET/Pore-Size/Pore-Volume measurements were performed on the modified MgO and standard MgO samples. All initial BET measurements were performed on the 120° C. oven-dried modified MgO samples (MGO-A, MGO-B, MGO-C, and MGO-D) under standard BET degassing protocols (5° C. heating up to 350° C., hold 16 hours). The spent BET samples were then used for further cyclic heat treatment. Each heat treatment cycle consisted of a 12 hour isothermal treatment at 550° C. ramped at 5° C./min in stagnant air and subsequent cooling to 120° C. BET measurements for all heat treated samples were performed without any further degassing (measured "as is").

As seen in FIG. 1, the most significant loss of surface area occurs on the very first cycle for all MgO samples, while subsequent exposures have relatively less impact. All treated samples show significant higher surface area improvement compared to the original sample. Samples MGO-A MGO-B and MGO-C show the surface area stabilizing impact by silica addition.

MgO is an ionic compound with an FCC (Face-Centered Cubic) structure. The point defects in the crystal structure for MgO are Schottky defects. Defects form when oppositely charged ions leave their lattice sites, creating vacancies. In the case of MgO, both oxygen and magnesium vacancies exist. However the sintering is controlled by the diffusion of oxygen vacancies. The addition of dopants like, NaF or LiF to MgO can positively adjust the ionic vacancy concentration, whereas $Al_2O_3$ or $SiO_2$ for example would act as an inhibitor for sintering. The addition of cations as dopants with a charge lower than +2 (NaF or LiF for example) will act to increase the sintering rate, whereas the addition of cations with a charge higher than +2 such as silica will inhibit it.

Colloidal silica addition to MgO in small quantities improves the surface area stability of MgO after multiple heat treatment cycles as shown in FIG. 1. It is interesting that the sodium silicate added sample MGO-D does not exhibit these characteristics since it contains $Na^+$, a cation that exhibits lower charge than that of $Mg^{2+}$, which is expected to have negative influences on maintaining surface area at elevated temperatures.

It has been observed that with the addition of a structure stabilizing agent, in the form of a compound or a mixture thereof, such as silica, alumina, or zirconia, thermal stability of the MgO tablets can be achieved. Structure stabilizing agents according to embodiments disclosed herein may include at least one of the following elements: Al, Si, Ti, Cr, Mn, Fe, Y, Zr, Mo and combinations thereof. For example, a structure stabilizing agent may be used in an amount ranging from about 0.04 to about 40% of the weight of the catalyst (based on a total weight of the structure stabilizing agent, the catalytic metal(s), and support material(s)). In some embodiments, the structure stabilizing agent is in the form of a binder including at least one of silica, alumina, and natural clays, such as kaolinite. In other embodiments, structure stabilizing agents may include at least one of $MgAlO_4$ and mixed metal oxides formed from the decomposition of Mg—Al hydrotalcites.

Magnesium oxide double-bond isomerization catalysts having an effective diameter of 5 mm or greater exhibit rapid deactivation in pilot testing. Such a rapid loss of activity, as either a fresh catalyst or a regenerated catalyst, renders the process economically less feasible and inhibits the wider use of magnesium oxide as an isomerization catalyst.

It is well known that smaller catalyst diameters may improve performance of a given catalyst by reducing the internal mass transfer resistances within the catalyst particle itself. Smaller diameter catalyst particles have shorter pores, and hence molecules have less distance to travel to reach active sites. Reducing the particle effective diameter is known to improve the overall activity of the catalyst within a reaction cycle.

The inventors of the present application have found unexpectedly that decreasing the effective diameter of the isomerization catalysts will, in fact, reduce the observed deactivation with time. Specifically, the inventors have found that a smaller effective diameter isomerization catalyst will reduce loss of surface area after subsequent regenerations, thus improving the overall performance. This is true both for metathesis where isomerization catalysts are used in combination and for isomerization alone. Advantages include longer isomerization catalyst cycle times, higher overall butenes conversion, and higher production, including higher propylene yields when used in a metathesis reactor in the presence of ethylene.

Figure 2A:
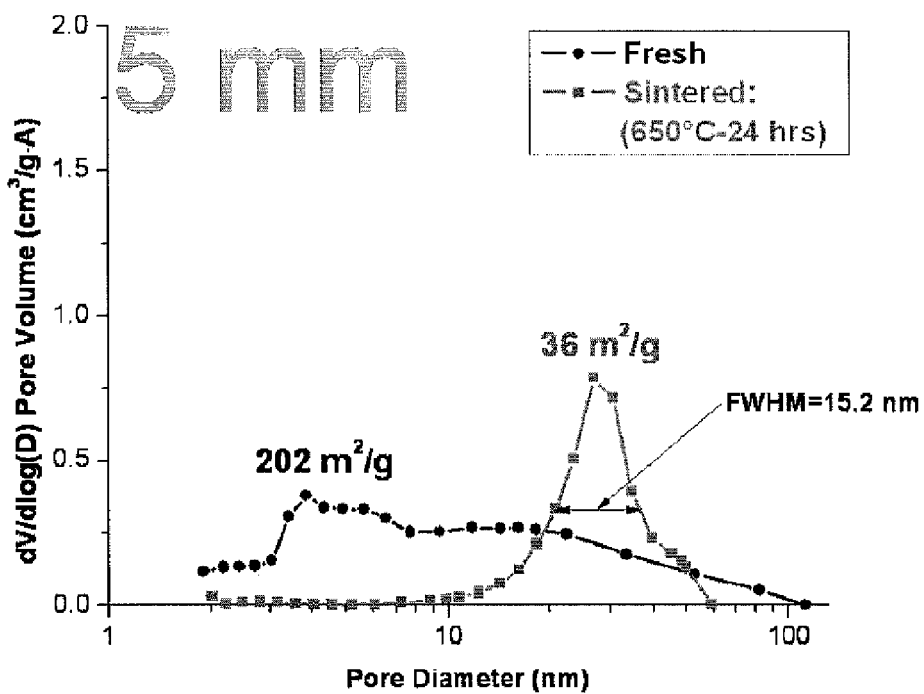
FIGS. 2A and 2B are graphical representations of changes in BET surface area and pore structure of MgO tablets of different sizes, after severe thermal aging at 650° C. (2A=5 mm, 2B=3 mm catalyst effective diameters).
Figure 2B:
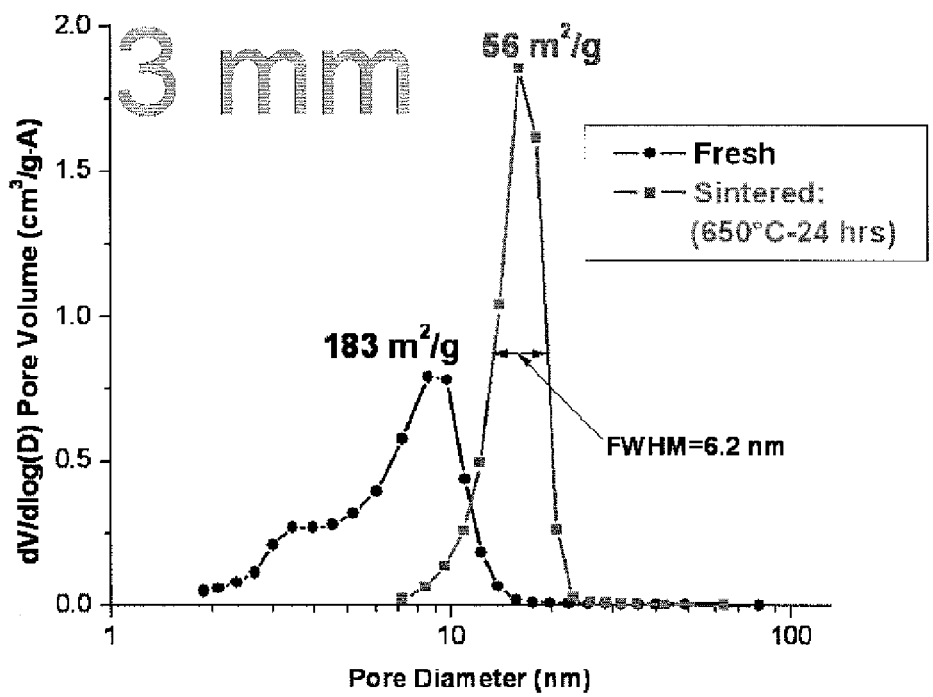

An unforeseen benefit of the smaller effective diameter is that the stability of the MgO catalyst can be improved even without the use of stabilizers. FIGS. 2A and 2B show the effect of thermal aging on BET surface area of the MgO catalyst at two different particle sizes, 5 mm and 3 mm, respectively. Thermal aging was carried out at 650° C. for a period of 24 h. Thermal aging at this high temperature of 650° C. is considered to be a severe thermal aging test for the MgO catalyst. It can be clearly seen that at the smaller particle size of 3 mm, the BET surface area of the catalyst was higher than that for the 5 mm particles by about 55%, (56 $m^2$/gm vs 36 $m^2$/gm) after the severe thermal aging.

The effect of the smaller effective diameter of the double-bond isomerization catalyst is two-fold. First, known higher activity is observed during the double-bond isomerization of butenes. However, unexpectedly, the stability of the catalyst is also improved leading to lower cycle to cycle deactivation. This directly translates to maintenance of catalyst performance over multiple cycles and therefore significantly increases the life of the catalyst.

Isomerization catalysts according to embodiments disclosed herein, such as magnesium oxide, may have an effective diameter of less than 5.0 mm; less than 4.0 mm in other embodiments; less than 3.2 mm in other embodiments; less than 3.0 mm in other embodiments; less than 2.8 mm in other embodiments; less than 2.5 mm in other embodiments; less than 2.0 mm in other embodiments; less than 1.75 mm in other embodiments; less than 1.5 mm in other embodiments; less than 1.4 mm in other embodiments; less than 1.0 mm in other embodiments; and less than 0.7 mm in yet other embodiments. The effective diameter of a catalyst particle is defined as the diameter of an equivalent sphere having a similar surface to volume ratio.

The isomerization catalysts according to embodiments disclosed herein may be in the form of pellets, extrudates, and the like. While powders are mentioned as a useful catalyst form in U.S. Pat. No. 6,875,901, because of high pressure drops associated with use of powders in fixed or packed beds, powders are not commercially used when isomerization catalysts are admixed with metathesis catalysts and used in the presence of ethylene in commercial fixed bed reactors or in fixed bed isomerization reactors. Accordingly, powders and finer material not typically used in a fixed bed reactor are specifically excluded from catalysts according to embodiments disclosed herein.

The isomerization catalysts according to embodiments disclosed herein are those that may be used with fixed bed reactors or formed as catalytic distillation structures, and thus isomerization catalysts in the form of pellets, spheres, extrudates, and the like, will typically have an effective diameter of at least 0.25 mm in other embodiments; at least 0.3 mm in other embodiments; at least 0.4 mm in other embodiments; and at least 0.5 mm in yet other embodiments, where the isomerization catalysts contain a stabilizing agent.

Further, isomerization catalysts according to embodiments disclosed herein are those that may be used with fixed bed reactors or formed as catalytic distillation structures, and thus isomerization catalysts in the form of pellets, spheres, extrudates, and the like, will typically have an effective diameter of at least 0.25 mm and having a maximum effective diameter of 4.0 mm when no stabilizing agent is employed; at least 0.5 mm in other embodiments and having a maximum effective diameter of 3.5 mm when no stabilizing agent is employed. Isomerization catalysts having the above described effective diameters may be produced in a number of manners. For example, catalyst spheres may be produced having an effective diameter according to embodiments described above. In other embodiments, a catalyst may be shaped to achieve a higher surface to volume ratio at a larger diameter. For example, a hollow cylinder, a tri-lobe particle, a shaped extrudate, or an extrudate of smaller diameter but larger length may be made. For example, star shaped extrudates similar to those disclosed in U.S. Pat. No. 7,351,393 may be used. These shaped catalysts have advantages in reducing pressure drops through fixed beds compared to spheres of equivalent effective diameter. In other embodiments, the isomerization catalyst may be deposited upon the surface of a support, forming an "eggshell" or thin layer of active ingredient upon a larger support (for eggshell catalysts, the effective diameter may be calculated relative to only the portion of the catalyst coated or impregnated with active material). These and other techniques may be used to reduce the effective diameter of isomerization catalysts according to embodiments disclosed herein.

Double-bond isomerization catalysts disclosed herein may be used for the conversion of various internal olefins, such as 2-butene, to an alpha-olefinic compound, such as 1-butene, in fixed bed reactors, distillation column reactors, and other reactors known in the art. While described below with respect to butenes, conversion of 2-pentene to 1-pentene, 2- or 3-hexene to 1-hexene, 2- or 3-heptene to 1-heptene, and the like are also contemplated. In particular, catalysts according to embodiments disclosed herein are useful in processes for the concurrent isomerization of 2-butene to 1-butene and metathesis of 2-butene with ethylene to form propylene, where the isomerization reaction may be performed in the presence of ethylene.

The mixed $C_4$ feed to processes disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene. In some embodiments, the mixed $C_4$ feed is pretreated to provide a normal-butene-rich feed for the metathesis reaction. For example, when butadiene is present in the $C_4$ feed, the butadiene may be removed via hydrogenation or extraction. In other embodiments, the mixed butenes feed following or in conjunction with butadiene hydrogenation may be subjected to hydroisomerization conditions to convert 1-butene to 2-butene, with isobutene being separated from a 2-butene stream by fractionation.

Ethylene and the normal butenes may then be fed to a reactor containing catalysts having both a metathesis functionality and an isomerization functionality, to convert at least a portion of the 1-butene to 2-butene, and to react the 2-butene with ethylene to form propylene as a metathesis product. The ethylene may be fed to the reactor at a rate to maintain a ratio of ethylene to n-butenes of at least 0.5; at least 1.0 in other embodiments; in the range from 0.5 to about 2.5 in other embodiments; and from about 1.0 or 1.5 to about 2.0 in yet other embodiments. The catalyst contained within the metathesis reactor may be any known metathesis catalyst, including oxides of Group VIB and Group VIIB metals on supports. Catalyst supports can be of any type and could include alumina, silica, mixtures thereof, zirconia, and zeolites. In addition to the metathesis catalyst, the catalyst contained in the metathesis reactor includes a double bond isomerization catalyst, such as magnesium oxide or calcium oxide, having an effective diameter as described above and in addition may or may not contain a stabilizing agent so as to maintain stable double-bond olefin isomerization activity over multiple cycles.

Figure 3:
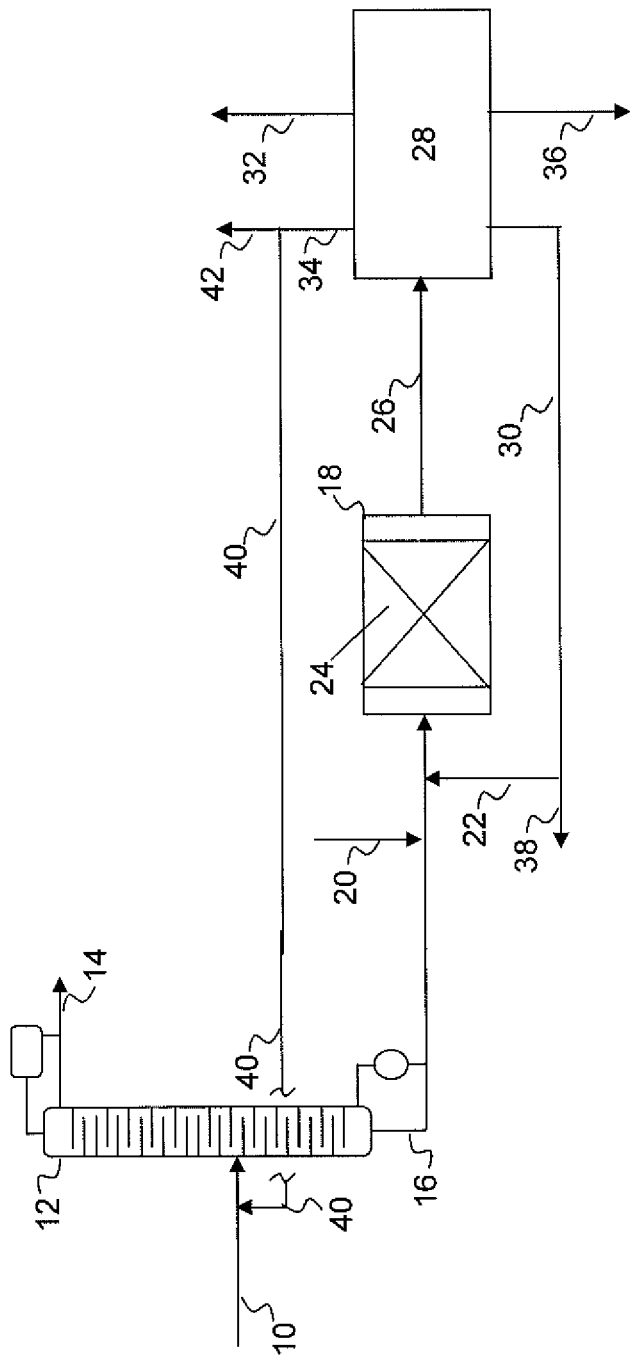
FIG. 3 is a simplified process flow diagram of a process for isomerization and metathesis using catalysts according to embodiments disclosed herein.

An example of a metathesis process for which catalysts according to embodiments disclosed herein may be useful is illustrated in FIG. 3. A mixed $C_4$ stream containing n-butenes, isobutene, and paraffins may be fed via flow line 10 to a separator 12, where the $C_4$s may be separated into at least two fractions, including a light $C_4$ fraction, including isobutene, and a heavy $C_4$ fraction, including n-butenes. The light $C_4$ fraction may be recovered from separator 12 as an overheads fraction via flow line 14.

The heavy $C_4$ fraction may be recovered as a bottoms fraction via flow line 16 and fed to metathesis reactor 18. Ethylene may be co-fed to reactor 18 via flow lines 20 and/or 22. Metathesis reactor 18 may contain one or more beds 24 of a conventional metathesis catalyst and isomerization catalysts according to embodiments disclosed herein. The metathesis and isomerization catalysts may be admixed in a single bed or may be placed in the reactor in series, such as by loading the catalysts sequentially in a single bed or placing the catalysts in the reactor as separate beds.

Effluent from metathesis reactor 18 may be fed via flow line 26 to a separation system 28, which may include, for example, distillation apparatus for separating the effluent into carbon number groups. As illustrated, separation system 28 may fractionate the metathesis product into at least four fractions, including an ethylene-containing fraction recovered via flow line 30, a propylene-containing fraction recovered via flow line 32, a $C_4$ fraction recovered via flow line 34, and a $C_{5+}$ fraction recovered via flow line 36.

A portion of the $C_2$ fraction recovered via flow line 30 may be purged from the system via flow line 38. If desired, at least a portion of the ethylene recovered via flow line 30 may be recycled as ethylene feed via flow line 22 to metathesis reactor 18.

At least a portion of the $C_4$ fraction recovered via flow line 34 may be recycled to separator 12 via flow line 40, and a portion may be purged, if necessary, via flow line 42. Although not illustrated, the $C_4$ fraction recovered via flow line 34 may alternatively be recycled to metathesis reactor 18 or to alternative downstream processing units. Additionally, when the hydrocarbon stream contains butane, the process may include a hydrogenation stage to hydrogenate at least a portion of the butadienes prior to fractionating the hydrocarbon feed in separator 12.

Isomerization catalysts according to embodiments disclosed herein may also be useful in other processes where the isomerization catalyst may be exposed to ethylene, such as may be disclosed in one or more of U.S. Pat. Nos. 6,777,582, 7,214,841, and 7,223,895, among others,

EXAMPLES

Silica was added to 5 mm commercial MgO tablets as a structure stabilizing agent. Silica in the form of a colloidal silica binder or as sodium silicate was added to the 5 mm MgO tablets. The thermal stability of the tablets were determined by measuring BET surface area of the 5 mm tablets after multiple thermal cycles. Each thermal cycle was performed by treating the tablets in air at 550° C. for a period of 12 h.

Example 1

Catalyst MGO-A was prepared by the wet impregnation of 5 mm MgO tablet (MGO) with a colloidal silica solution containing 30 wt % silica (Ludox, AS-30, Aldrich chemicals). After the impregnation, the catalyst was dried at 120° C. for 24 h. The silica content of MGO-A was measured by XRF to be 0.81 wt %. Initial BET surface area was measured after a standard BET degassing at 350° C. for 16 h. Thermal cycling was carried out at 550° C. for 12 h. After each heat treatment the catalyst was cooled to 120° C. for 12 h before the next thermal cycle. FIG. 1 shows the BET surface area decrease for catalyst MGO-A after the thermal aging. Significant reduction in BET surface area is observed after the first thermal cycle. However, after the second thermal cycle, the BET surface area of MGO-A stabilizes. In comparison, the untreated 5 mm MgO tablet (MGO) still continues to lose BET surface area after every cycle, up to the $4^{th}$ thermal cycle.

Example 2

Catalyst MGO-B was prepared in a similar manner to catalyst MGO-A by the wet impregnation of 5 mm MgO tablet (MGO) with a colloidal silica solution containing 30 wt % silica (Ludox, AS-30, Aldrich chemicals). After the impregnation, the catalyst was dried at 120° C. for 24 h. The silica content MGO-B was measured by XRF to be 0.81 wt %. Initial BET surface area was measured after a standard BET degassing at 350° C. for 16 h. Thermal cycling was carried out at 550° C. for 12 h. After each heat treatment the catalyst was cooled to 120° C. for 12 h before the next thermal cycle. FIG. 1 shows the BET surface area decrease for catalyst X052-L2 after the thermal aging. Significant reduction in BET surface area is observed after the first thermal cycle. However, after the second thermal cycle, the BET surface area of MGO-B stabilizes. In comparison, the untreated 5 mm MgO tablet (MGO) still continues to lose BET surface area after every cycle.

Example 3

Catalyst MGO-C was prepared in a similar manner to examples 1 and 2 by the wet impregnation of 5 mm MgO tablet (MGO) with a colloidal silica solution containing 30 wt % silica (Ludox, AS-30, Aldrich chemicals). After the impregnation, the catalyst was dried at 120° C. for 24 h. The silica content MGO-C was measured by XRF to be 1.14 wt %. Initial BET surface area was measured after a standard BET degassing at 350° C. for 16 h. Thermal cycling was carried out at 550° C. for 12 h. After each heat treatment the catalyst was cooled to 120° C. for 12 h before the next thermal cycle. FIG. 1 shows the BET surface area decrease for catalyst MGO-C after the thermal aging. Significant reduction in BET surface area is observed after the first thermal cycle. However, after the second thermal cycle, the BET surface area of MGO-C stabilizes. In comparison, the untreated 5 mm MgO tablet (MGO) still continues to lose BET surface area after every cycle.

Example 4

Catalyst MGO-D was prepared by the wet impregnation of 5 mm MgO tablet (MGO) with a solution of sodium silicate. After the impregnation, the catalyst was dried at 120° C. for 24 h. The silica content MGO-D was measured by XRF to be 1.40 wt %. Initial BET surface area was measured after a standard BET degassing at 350° C. for 16 h. Thermal cycling was carried out at 550° C. for 12 h. After each heat treatment the catalyst was cooled to 120° C. for 12 h before the next thermal cycle. FIG. 1 shows the BET surface area decrease for catalyst MGO-D after the thermal aging. Significant reduction in BET surface area is observed after the first thermal cycle. MGO-D continues to lose BET surface area in every cycle up to the $4^{th}$ thermal cycle. MGO-D contains $Na^+$, a cation that exhibits lower charge than that of $Mg^{2+}$, which is expected to have negative influences on maintaining surface area at elevated temperatures. MGO-D is similar to the 5 mm MgO tablet (MGO) which also continues to lose BET surface area after every cycle.

As described in the examples above, structure stability of the MgO tablet can be improved by adding a structure stabilizing agent.

It has also been found that using a smaller effective diameter, the stability of the MgO catalyst can be improved even without adding a stabilizing agent. Thermal aging was carried out at 650° C. for a period of 24 h. Thermal aging at this higher temperature of 650° C. is considered to be a severe thermal aging test for the MgO catalyst.

Example 5

A 5 mm MgO tablet prepared without using a stabilizing agent was subjected to severe thermal aging by treating the tablet at 650° C. for a period of 24 h. FIG. 2 shows the change in the pore volume as well as the BET surface area of the tablet after the severe thermal aging. Initial BET surface area of the 5 mm MgO tablet was 202 $m^2/g$ and after the thermal aging, the surface area reduced to 36 $m^2/g$. Also, the average pore diameter increased to about 28 nm from a broader range but smaller diameter from 3-10 nm. After thermal aging the full width at half maximum (FWHM) was measured to be 15.2 nm.

Example 6

A 3 mm MgO tablet prepared using the identical MgO and no stabilizing agent. It was then subjected to severe thermal aging by treating the tablet at 650° C. for a period of 24 h. FIG. 2 shows the change in the pore volume as well as the BET surface area of the tablet after the severe thermal aging. Initial BET surface area of the 5 mm MgO tablet was 183 $m^2/g$ and after the thermal aging, the surface area reduced to 56 $m^2/g$. Also, the average pore diameter increased to about 18 nm from a smaller diameter of about 8 nm. After thermal aging the full width at half maximum (FWHM) was measured to be 6.2 nm. Comparing the 5 mm MgO tablet in Example 5 with the 3 mm MgO tablet in Example 6, the smaller effective diameter tablet retains a higher BET surface area after the severe thermal aging treatment. Also, the average pore diameter after the thermal aging is lower with the 3 mm tablet compared to the 5 mm tablet. The pore distribution is also narrower with the 3 mm MgO tablet after the thermal aging compared to the 5 mm MgO tablet, as seen by the differences in the full width at half maximum (FWHM) for the two sizes. 3 mm tablet shows a FWHM of 6.2 nm compared to a FWHM of 15.2 for the 5 mm tablet.

As described in the examples above, improvements in MgO catalyst stability is achieved by utilizing a catalyst of lower effective diameter.

The performance of magnesium oxide catalysts according to embodiments disclosed herein is compared to the performance of conventional magnesium oxide catalysts, each in the presence of ethylene for the isomerization of 1-butene to 2-butene without methathesis catalyst. In addition to comparing catalysts, it is noted that the isomerization reaction is equilibrium limited; at equilibrium, a C4 feed of pure 2-butene would exhibit a conversion of approximately 72 to 75 percent when operated at a temperature of 600° F. This corresponds to a 2-butene/1-butene equilibrium ratio of approximately 3.6 at reaction temperature. Similarly a feed of pure 1 butene would exhibit a conversion of approximately 22% to reach that same equilibrium ratio.

Example 7

A magnesium oxide catalyst is prepared as a 5 mm pellet, having a length to diameter ratio of 5.5. The catalyst is loaded into an isomerization reactor and heated in a dry inert atmosphere at 350° C. for 60 hours to remove substantially all activity-affecting amounts of water and carbon dioxide.

The catalyst is then tested for isomerization activity for the isomerization of 1-butene to 2-butene in the presence of ethylene. The isomerization reaction is conducted at 400 psig and 600° F. and a weight hourly space velocity (WHSV) of 5.4. Ethylene and 1-butene are fed to the reactor at a ratio of 1.8:1 ethylene to 1-butene.

Figure 4:
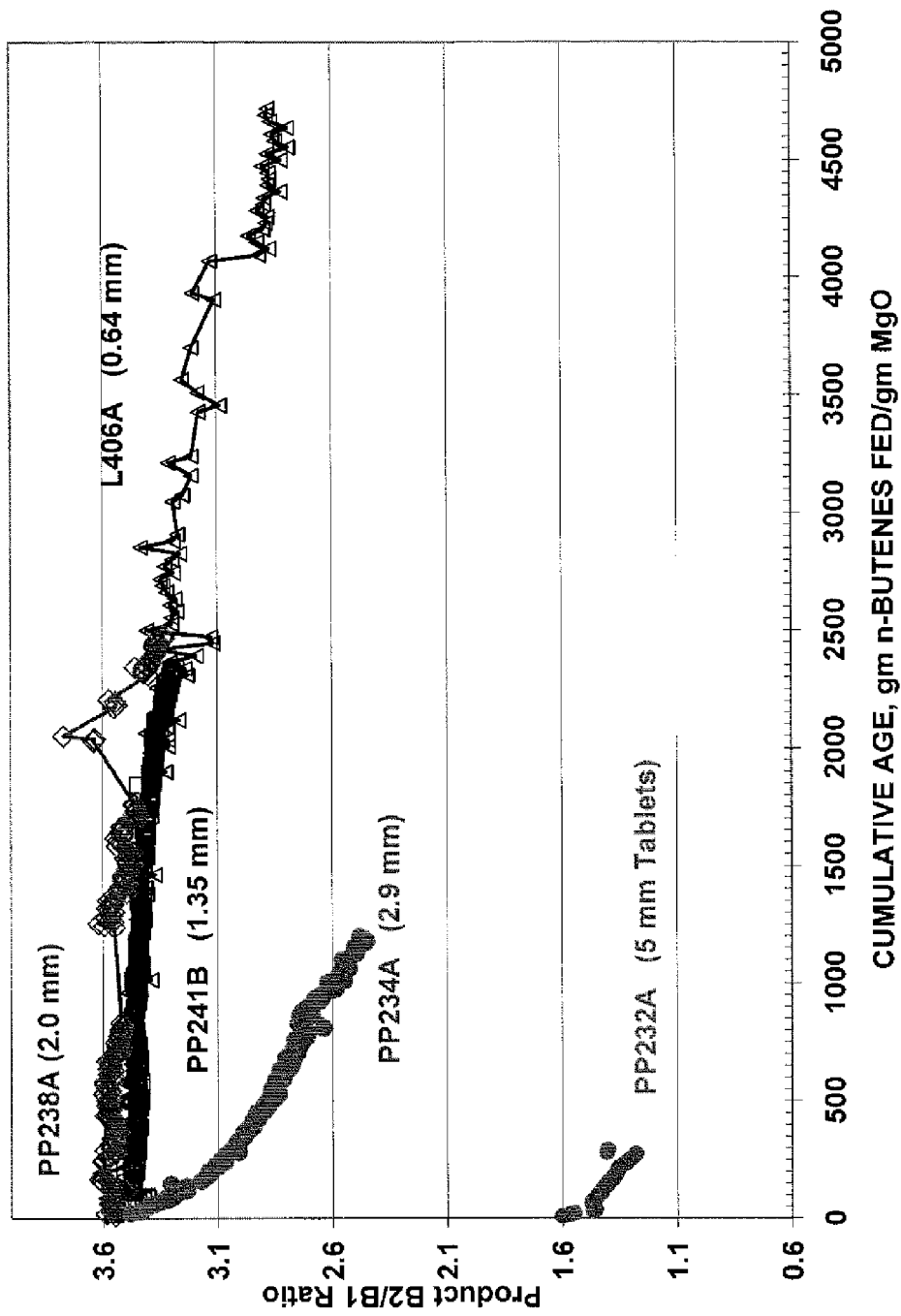
FIG. 4 is a graphical illustration of catalyst activity over time for catalysts according to embodiments disclosed herein as compared to typical magnesium oxide catalysts when used in the presence of ethylene.

Results of the experiment are presented in FIG. 4. Starting with pure 1 butene (a 2 butene/1 butene ratio of 0) as shown in FIG. 4, even at a lower WHSV, the catalyst fails to reach equilibrium initially, reaching a 2-butene to butene 1 ratio of only 1.5. The activity of the catalyst decreases rapidly with cumulative age.

Example 8

A magnesium oxide catalyst is prepared having an effective diameter of 2.9 mm (6 by 8 mesh). The catalyst is loaded into an isomerization reactor and heated in a dry inert atmosphere at 350° C. for 60 hours to remove substantially all activity-affecting amounts of water and carbon dioxide.

The catalyst is then tested for isomerization activity for the isomerization of 1-butene to 2-butene in the presence of ethylene. The experiment was carried out in an identical manner to example 7.

Results of the experiment are also presented in FIG. 4. Under similar conditions, a catalyst having a smaller effective diameter, 2.9 mm, may initially reach equilibrium, but activity falls off rapidly with time.

Example 9

A magnesium oxide catalyst is prepared having an effective diameter of 1.35 mm (12 by 18 mesh). The catalyst is loaded into an isomerization reactor and heated in a dry inert atmosphere at 350° C. for 60 hours to remove substantially all activity-affecting amounts of water and carbon dioxide.

The catalyst is then tested for isomerization activity for the isomerization of 1-butene to 2-butene in the presence of ethylene. The isomerization reaction is conducted at conditions identical to those of Examples 7 and 8.

Results of the experiment are also presented in FIG. 4. As can be seen in FIG. 4, the catalyst particles having an effective diameter of 1.35 mm reaches equilibrium initially, having a product 2-butene to 1-butene ratio of about 3.5. Additionally, the smaller effective diameter catalyst maintains activity/performance over an extended period of time, decreasing to a product 2-butene to 1-butene ratio of about 3.3 after a cumulative age of approximately 2400 grams n-butenes fed per gram of magnesium oxide.

Example 10

A magnesium oxide catalyst is prepared having an effective diameter of 0.64 mm (20 by 10 mesh). The catalyst is loaded into an isomerization reactor and heated in a dry inert atmosphere at 350° C. for 60 hours to remove substantially all activity-affecting amounts of water and carbon dioxide.

The catalyst is then tested for isomerization activity for the isomerization of 1-butene to 2-butene in the presence of ethylene. The isomerization reaction is conducted at conditions identical to Examples 7-9.

Results of the experiment are also presented in FIG. 4. As can be seen in FIG. 4, the catalyst particles having an effective diameter of 0.64 mm reaches equilibrium initially, having a product 2-butene to 1-butene ratio of about 3.5. Additionally, the smaller effective diameter catalyst maintains activity/performance over an extended period of time, decreasing to a product 2-butene to 1-butene ratio of about 3.2 after a cumulative age of approximately 4000 grams n-butenes fed per gram of magnesium oxide.

One skilled in the art may expect that catalysts having a smaller effective diameter would improve the kinetics for isomerization of 1-butene to 2-butene, as based on reduced mass transfer limitations. The reduced mass transfer resistance would lead to behavior as observed above, namely an increase in activity allowing for isomerization to reach equilibrium for a longer time.

As described above however, improvements in catalyst activity over multiple cycles in addition to activity within a cycle were unexpectedly observed with MgO catalysts with smaller effective diameter.

It has been found that using a smaller effective diameter, the stability of the MgO catalyst can be improved. It has also been found that using a smaller effective diameter, the stability of the MgO catalyst to withstand cycle to cycle regeneration can be improved. 5 mm MgO tablets and 3 mm MgO tablets without stabilizing agents added were both tested under metathesis conditions to produce propylene, which include both isomerization of 1-butene to 2-butene and the metathesis of ethylene and 2-butene to form propylene As the metathesis reaction occurs only between 2 butene and ethylene (1 butene and ethylene being a non-productive reaction), using a feed consisting of only ethylene and 1 butene will provide the greatest required isomerization duty to reach a given metathesis conversion. Further, depending upon the feed purity, there would be additional interconversion between 1 and 2 butene, resulting in a ratio of 2-butene to 1-butene of approximately 3.6 in the effluent if equilibrium is attained. This ratio would decrease as the isomerization catalyst ages both within a cycle and over multiple cycles if the feedstock was richer in 1 butene than the equilibrium ratio at reaction temperature.

Example 11

The tests were carried out in a mixed bed containing the MgO tablets for isomerization and a $WO_3/SiO_2$ catalyst for metathesis. The tests were conducted at a temperature of 315° C., a WHSV of 12, and at a pressure of 400 psig. The feedstock consisted of pure 1 butene and ethylene in a molar ratio of ethylene/1 butene of 1.8. Two catalysts were prepared in an identical manner with the exception that one was tableted to an effective diameter of 3 mm and the other to an effective diameter of 5 mm. They were then each subjected to an identical testing protocol. The testing protocol consisted of the following sequence:
1. The catalyst was activated and subjected to a reaction cycle at 315° C. as described above. The test was allowed to run until deactivation was noted as evidenced by a loss of 1 butene conversion.
2. The catalyst was regenerated by burning the coke deposited at a temperature of 500° C. followed by a $N_2$ purge at 550° C. The catalyst was then cooled and activated for the next reaction cycle.
3. A second reaction cycle of 24 hours was completed to deposit some coke on the catalyst. After 24 hours this catalyst was regenerated as in step 2.
4. Step 3 was repeated 2 additional times to thus result in the catalyst mixture having experienced a total of 4 cycles to that point.
5. A fifth reaction cycle was then completed allowing the reaction to run until deactivation was noticed as evidenced by a loss of 1 butene conversion.

1-Butene conversion during both cycle 1 and cycle 5 is shown for both the 3 mm MgO tablet and the 5 mm tablet in FIG. 5. Conversion is shown on a relative 1-butene conversion basis. For reference, the equilibrium 1-butene conversion is shown as the relative conversion of 1.0.

It can be seen that the cycle 1 performance of the 3 mm MgO tablet was close to equilibrium and stable up to a cumulative age of 1200 kg n-butenes fed/kg catalyst. With further increase in cumulative age, catalyst deactivation was observed and at a cumulative age of 2600 kg n-butenes fed/kg catalyst, 0.66 relative 1-butene conversion was observed. It can further be seen that the cycle 5 performance of the 3 mm MgO tablet was slightly below equilibrium and very similar to the cycle 1 conversion. Also, 1-butene conversion for cycle 5 was stable up to a cumulative age of 1100 kg n-butenes fed/kg catalyst. With further increase in cumulative age, catalyst deactivation was observed and at a cumulative age of 1800 kg n-butenes fed/kg catalyst, 0.81 relative 1-butene conversion was observed.

For the 5 mm tablet, it can be seen that the cycle 1 performance of the 5 mm MgO tablet was well below equilibrium (relative 1-butene conversion of 0.91). Also, 1-butene conversion for cycle 1 on the 5 mm MgO tablet was significantly lower than that for the cycle 1 on the 3 mm MgO tablet throughout the test. The deactivation rate of the 5 mm MgO tablet was also much higher than that for the 3 mm MgO tablet, in their respective first cycles. 1-Butene conversion for the 5 mm MgO in cycle 1 was never stable and continuously deactivation from the start of run. At a cumulative age of 1975 kg n-butenes fed/kg catalyst, only 0.46 relative 1-butene conversion was observed.

It can be seen that the cycle 5 performance of the 5 mm MgO tablet was also well below equilibrium (relative 1-butene conversion of 0.90). The deactivation rate of the 5 mm MgO tablet was also much higher than that for the 3 mm MgO tablet, in their respective fifth cycles. The deactivation rate of the 5 mm MgO tablet in cycle 5 was also significantly higher than that in its first cycle. This is clearly significantly different from the cycle 5 results for the 3 mm MgO tablet. The deterioration in catalyst performance from cycle 1 to cycle 5 was much worse in the case of the 5 mm MgO tablet, compared to the 3 min MgO tablet. At a cumulative age of 1044 kg n-butenes fed/kg catalyst, only 0.44 relative 1-butene conversion was observed.

One skilled in the art may expect that catalysts having a smaller effective diameter would improve the kinetics for isomerization of 1 butene to 2-butene, as based on reduced mass transfer limitations. This would explain the differences in performance between the 3 mm and 5 mm effective diameter for cycle 1. However, unexpectedly there was also a significant reduction in the deactivation rates during a cycle were observed with MgO catalysts with smaller effective diameter. It was also observed that cycle to cycle performance deterioration is reduced by using a catalyst with a smaller effective diameter. This can not be explained by a simple reduction in mass transfer resistances for lower effective diameters.

As described above, embodiments disclosed herein provide catalysts for the isomerization of 1-butene to 2-butene and metathesis 2-butene and ethylene to form propylene. Isomerization catalysts disclosed herein, having an effective diameter of less than about 3.2 mm, may exhibit excellent activity for the isomerization of 1-butene to 2-butene, even in the presence of ethylene. Additionally, such catalysts show reduced deactivation rates over time and longer catalyst life, in the presence of ethylene. Advantageously, catalysts according to embodiments disclosed herein may improve the overall performance of the combined isomerization/metathesis reactor, including longer isomerization catalyst cycle times, higher overall butenes conversion, and higher production, including higher propylene yields when used in a metathesis reactor in the presence of ethylene.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the double-bond isomerization of olefins, the process comprising:
    contacting a fluid stream comprising olefins with a fixed bed comprising an activated basic metal oxide isomerization catalyst comprising a structure stabilizing agent, to convert at least a portion of the olefin to its isomer;
wherein a process for preparing the isomerization catalyst comprises coextruding an admixture of the basic metal oxide and colloidal silica.

2. The process of claim 1, wherein the basic metal oxide isomerization catalyst comprises at least one of magnesium oxide, calcium oxide, strontium oxide, barium oxide, lithium oxide, and combinations thereof.

3. The process of claim 1, wherein the basic metal oxide isomerization catalyst comprises magnesium oxide.

4. The process of claim 1, wherein the structure stabilizing agent comprises at least one of elements Al, Si, Ti, Cr, Mn, Fe, Y, Zr, Mo, and combinations thereof.

5. The process of claim 1, wherein the catalyst comprises 0.04 weight % to 40 weight % of the structure stabilizing agent.

6. The process of claim 1, wherein the structure stabilizing agent is in the form of a binder comprising at least one of silica, alumina, and natural clays.

7. The process of claim 1, wherein the basic metal oxide isomerization catalyst has an effective diameter in the range from about 0.25 mm to about 5.0 mm.

8. The process of claim 1, wherein the basic metal oxide isomerization catalyst has an effective diameter in the range from about 0.5 mm to about 3.2 mm.

9. The process of claim 1 wherein the basic metal oxide isomerization catalyst is in the form of a tablet or an extrudate.

10. The process of claim 1, wherein an initial activity of the basic metal oxide isomerization catalyst is a 2-butene to 1-butene product ratio of at least 3.0, as measured by conversion of pure 1-butene to 2-butene in the presence of at least an equimolar amount of ethylene at a temperature of 600° F. and a pressure of 400 psig.

11. A process for the double-bond isomerization of olefins, the process comprising:
contacting a fluid stream comprising olefins with a fixed bed comprising an activated basic metal oxide isomerization catalyst having an effective diameter in the range of 0.25 mm to 4.0 mm to convert at least a portion of the olefin to its isomer;
wherein a process for preparing the isomerization catalyst comprises coextruding an admixture of the basic metal oxide and colloidal silica.

12. The process of claim 11, wherein the basic metal oxide isomerization catalyst comprises at least one of magnesium oxide, calcium oxide, strontium oxide, barium oxide, lithium oxide, and combinations thereof.

13. The process of claim 11, wherein the basic metal oxide isomerization catalyst comprises magnesium oxide.

14. The process of claim 11, wherein the effective diameter of the basic metal oxide isomerization catalyst is in the range from about 0.5 mm to about 3.2 mm.

15. The process of claim 11 wherein the basic metal oxide isomerization catalyst is in the form of a tablet or an extrudate.

\* \* \* \* \*